United States Patent [19]

Pinchuk et al.

[11] Patent Number: 4,738,740
[45] Date of Patent: Apr. 19, 1988

[54] METHOD OF FORMING IMPLANTABLE VASCULAR GRAFTS

[75] Inventors: Leonard Pinchuk; John B. Martin, Jr., both of Miami, Fla.

[73] Assignee: Corvita Corporation, Miami, Fla.

[21] Appl. No.: 800,524

[22] Filed: Nov. 21, 1985

[51] Int. Cl.$^4$ .................... B65H 81/00; B29D 23/00; A61F 1/02

[52] U.S. Cl. ................. 156/167; 156/273.1; 264/24

[58] Field of Search .................. 156/167, 175, 273.1; 623/1; 264/22, 24, 205, 204, 10

[56] References Cited

U.S. PATENT DOCUMENTS

| | | |
|---|---|---|
| 2,411,660 | 11/1946 | Manning . |
| 2,886,877 | 5/1959 | Frickert et al. . |
| 4,044,404 | 8/1977 | Martin et al. . |
| 4,323,525 | 4/1982 | Bornat . |
| 4,475,972 | 10/1984 | Wong . |

FOREIGN PATENT DOCUMENTS 0009941  4/1980  European Pat. Off. .

OTHER PUBLICATIONS

Article, Annis, et al, "An Elastomeric Vascular Prosthesis", Trans. Am. Soc. Artif. Intern. Organs, vol. XXIV, pp. 209-214 (1978).

Leidner et al, "A Novel Process for the Manufacturing of Porous Grafts: Process Description and Product Evaluation", Journal of Biomedical Materials Research, vol. 17, pp. 229-247 (1983).

Primary Examiner—Michael Ball
Attorney, Agent, or Firm—Lockwood, Alex, Fitzgibbon & Cummings

[57] ABSTRACT

Vascular grafts are provided that have an external surface which has a porous structure that is conducive to tissue ingrowth thereinto after the vascular graft has been implanted. The vascular graft is prepared by winding an extruded fiber onto a mandrel in the presence of intermittently applied electrostatic forces. Such vascular graft may include an internal surface that was formed under the influence of the electrostatic charge, which internal surface has a porosity that is substantially less than that of said porous external surface.

13 Claims, 1 Drawing Sheet

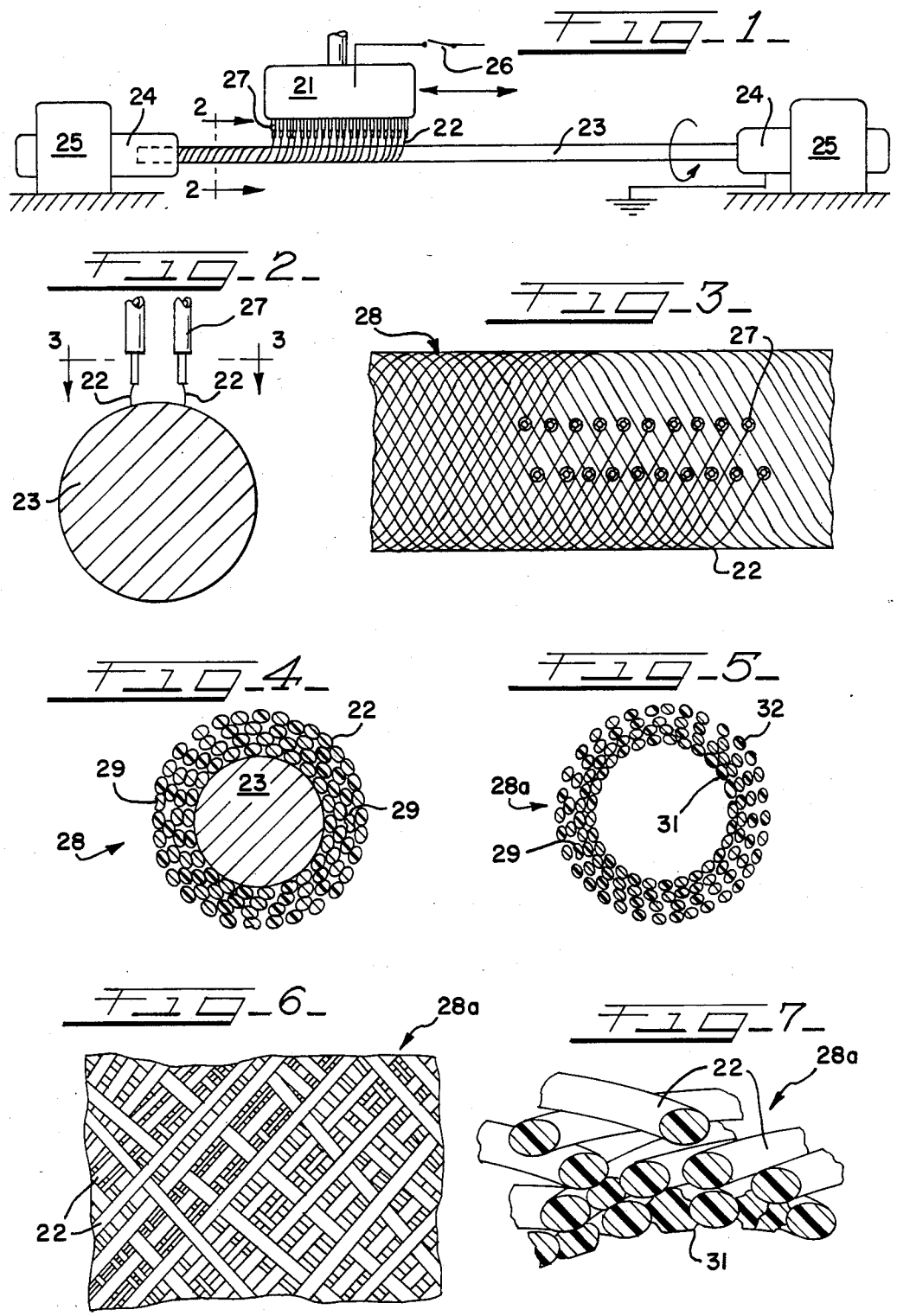

METHOD OF FORMING IMPLANTABLE VASCULAR GRAFTS

BACKGROUND AND DESCRIPTION OF THE INVENTION

The present invention generally relates to vascular grafts that have outside surfaces which have porous structures, the vascular grafts being of the non-braided and non-woven type and having an outside surface porosity that provides an environment which is conducive to tissue ingrowth into the pores of the porous surface. The vascular grafts are formed from a fiber forming polymer which is extruded into fibers that are wound or spun onto a mandrel while being intermittently subjected to electrostatic charge conditions. Typically, breaks occur in the formed fiber during spinning, and the broken fiber is readily reattached at or near its point of breakage with the aid of the electrostatic conditions. Such electrostatic conditions help to provide vascular grafts with good interfiber bonding and closely controlled pore sizes, especially by providing internal surfaces that are exceptionally smooth and that have low porosity or substantially no porosity, as desired.

Vascular grafts are known to be made by methods which include winding extruded material onto a mandrel in an attempt to provide a degree of porosity that is desired for implantable vascular grafts, especially including providing an ingrowth environment that is particularly suitable for promoting tissue ingrowth at the implantation locations. One such approach is detailed in U.S. Pat. No. 4,475,972, the disclosure of which is incorporated by reference hereinto. That patent describes non-woven vascular grafts that are made by extruding a polyurethane solution under pressure through an opening and then drawing the extruded material while winding same on a mandrel.

In practicing methods such as those of this patent, certain problems have been encountered. It is not always possible to adequately control the extruded fibers in order to obtain both small pore size and good adhesion between connecting spun fibers. It is particularly difficult to achieve adequate bonding of the first few graft layers, which contributes to subsequent tearing thereof during mandrel removal, both of which result in the production of vascular grafts that have internal surfaces which are uneven and scraggly with torn fibers extending into the lumen of the graft. It is typically very desirable that vascular grafts have an internal surface that is substantially smooth and as free of obstructions as possible in order to thereby provide flow-through conditions that are substantially optimum for the internal diameter of the vascular graft.

When making these types of wound spun fiber vascular grafts, the fibers often break during the spinning operation, especially when, as is usually preferred, the spun fibers are drawn longitudinally during spinning, which exerts a force on the freshly extruded and as yet only partially set filament in a manner that tends to occasionally break the filament. When such fiber breakage occurs under these circumstances or any other circumstances (such as inertial effects, bubbles in polymer or the like), it is typically necessary to stop the relative movement between the extrusion device and the mandrel and to manually reattach the broken fiber end to the remainder of the fiber(s) on the mandrel or to the mandrel itself.

Besides being labor intensive and time-consuming and potentially leading to production down-time, this need for manual reattachment often leads to poor fiber adhesion at the plane of reattachment, which can lead to graft delamination. Fiber breaks that are reattached according to previously known methods include reattaching the fiber at the ends of the graft, which ends are later cut off and discarded. This procedure to manually reattach a fiber without breaking other fibers is of such a long duration that the underlying fiber layer dries out and does not bond well to subsequent layers. Uniformity of spun strands can thus be disrupted, leading to potential points of weakness or unsightly sections of the completed vascular graft. This is especially important for vascular tubes that are intended for arterial use inasmuch as arterial prostheses should be able to withstand pulsatile arterial blood pressures of at least 300 mm Hg, preferably greater than 500 mm Hg, for prolonged periods of time of on the order of ten years and more.

Included in the objectives of providing vascular grafts having porous surfaces is to promote, after implantation of such a graft, colonization and tissue ingrowth into the depth of the porous surface from adjacent body tissue in order to provide bonding between the body tissue host and the porous vascular graft. Typically, the body tissue ingrowth is combined with the promotion of tissue growth into the porous surface from nucleated bloodstream cells. Such porous surfaces provide a porous depth that affords a means for fixation to host tissues by soft tissue ingrowth into the porous depth of the surface, and they provide tissue-implant interfaces which are blood compatible arising from colonization and tissue formation on the blood-contacting surfaces of the vascular grafts. Tissue ingrowth is desired on the external surface. Desired on the internal surface is endothelium cell ingrowth which is provided by nucleated blood cells. Accordingly, it is important that such vascular grafts be provided with porosity and that the parameters of such porosity be closely controlled during manufacture of the vascular grafts in order to achieve the desired extent of ingrowth after implantation.

Disadvantages of the type hereinbefore discussed have been substantially eliminated by proceeding in accordance with the present invention, which also provides vascular grafts that are formed under closely controlled conditions whereby the porosity can be varied from layer to layer while also being accurately and consistently formed. For example, the present invention achieves fiber break reattachment while minimizing the chance of forming undesirable delamination sites. The invention also facilitates the formation of a vascular graft having a substantially smooth inner surface that is of low porosity or that is substantially non-porous. Also, an electrostatic field is used to provide a well-bonded layer on the outside of the graft to prevent scraggylness of the graft from handling during implantation. A single pass on the outside of the graft provides a "hair net" effect without affecting the pore size.

In summary, the present invention includes vascular grafts that are made by extruding a fiber forming polymer while winding same on a mandrel and while intermittently applying an electrostatic charge between the extrusion device and the mandrel in order to accelerate the movement of the fiber forming polymer strand toward the mandrel. Typically, the electrostatic charge is applied during extrusion and winding of the first or innermost spinning passes in order to provide a vascular graft having a substantially smooth interior surface and low porosity inner layer or layers. Electrostatic charge application at the times of fiber breakage during any portion of the spinning operation accelerates the broken fiber from the extruder and onto the mandrel at or near the location of breakage and before the broken ends have set to such a degree that smooth reattachment is no longer possible.

It is accordingly a general object of the present invention to provide an improved non-woven vascular graft.

Another object of the present invention is to provide an improved vascular graft having an exterior surface that promotes tissue ingrowth thereinto and having an internal surface of reduced porosity that allows cellular ingrowth when compared with the external surface.

Another object of this invention is to provide an improved vascular graft that includes the extrusion and winding of a fiber forming polymer onto a mandrel while applying an electrostatic charge in order to accelerate the forming fiber onto the mandrel at selected times.

Another object of the present invention is to provide an improved vascular graft and the production thereof by a process including the intermittent application of electrostatic energy between a mandrel and an extruder for a fiber forming polymer.

Another object of the present invention is to provide an improved process for the production of vascular grafts which includes closely controlling the porosity of various layers of the grafts.

Another object of the present invention is to provide an improved process for manufacturing non-woven vascular grafts and which includes electrostatically repairing breaks in fiber forming polymer extrusions.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a generally schematic sketch illustrating a step in the manufacture of the vascular graft in accordance with this invention;

FIG. 2 is a cross-sectional view taken along the line 2—2 of FIG. 1;

FIG. 3 is a cross-sectional view along the line 3—3 of FIG. 2;

FIG. 4 is a cross-sectional view illustrating a vascular graft prepared according to a process employing electrostatic repair but without extensive electrostatic charge application when the internal layers were wound;

FIG. 5 is a cross-sectional view similar to FIG. 4 and which generally illustrates results obtained by the electrostatic acceleration of the film-forming polymeric extrudate during the interior windings;

FIG. 6 is a sketch of an exploded view of an external surface of a vascular graft prepared in accordance with the present invention at a magnification of on the order of about 150 times; and FIG. 7 is a sketch of a cross-section of a vascular graft in accordance with the present invention and at an approximate magnification of about 1000 times.

DESCRIPTION OF THE PARTICULAR EMBODIMENTS

Regarding the apparatus illustrated in FIG. 1, which is suitable for carrying out the process according to the present invention, such includes a distributor 21 for achieving formation of polymeric fibers 22, typically in conjunction with formation of those fibers from a fiber forming polymeric solution by extrusion techniques. Before such fibers are fully set, they are wound onto a mandrel 23, which is typically rotated within suitable jaws 24. In the arrangement illustrated, the distributor 21 moves back and forth within a plane generally between the jaws 24, while the mandrel 23 is rotated by suitable means such as the illustrated motors 25. Alternatively, the distributor 21 can take the form of a spinnerette that rotates around the mandrel 23. Whatever mechanism or technique is utilized, such will result in combined rotational and translational relative movement between the polymeric fibers 22 and the mandrel 23. A desired number of layers of polymeric fibers 22 are laid down over the mandrel 23.

Electrostatic charge generation components are included in order to develop an electrostatic charge between the distributor 21 and the mandrel 23. Preferably, the mandrel 23 is grounded or negatively charged, while the distributor 21 is positively charged when a switch 26 or the like is closed. Alternatively, the distributor can be grounded and the mandrel can be positively charged. When this electrostatic charge is present, the polymeric fibers 22 accelerate from the distributor 21 to the mandrel 23 to a speed that is faster than that which is achieved during spinning and drawing in the absence of the electrostatic field. Also, when the electrostatic field is applied, adjacent polymeric fibers 22, each of which carry a like charge, tend to bow away from each other as generally illustrated in FIG. 2. Distributor 21 may include any number of individual extrusion orifices or hypodermic cylinders 27 as illustrated in FIGS. 1, 2 and 3.

Polymeric fibers 22, when set, form a generally cylindrical elongated vascular graft 28, such as is illustrated in FIG. 4, which has an inside diameter that is substantially the same as the outside diameter of the mandrel 23. Individual fibers 22 are bound to each other, generally at most if not substantially all of the locations where the fibers intersect or otherwise contact each other. This fiber-to-fiber bonding results when the solvent-containing and only partially set fibers 22 engage one another during winding, which is typically facilitated by drawing the extruded fibers over fibers lying thereunder, such being suitably accomplished by selecting an appropriate speed of relative movement between the mandrel 23 and the distributor 21 which will draw the fibers 22 at a speed that is faster than the rate by which they are extruded from the distributor 21.

Such winding, and particularly the drawing of the fibers 22 as well as the inertial effects of accelerating or decelerating the distributor during reversal of the shuttle carrying the distributor 21, tends to occasionally result in breakage of fibers. Fiber breakage is remedied by applying the electrostatic charge as soon as breakage occurs in order to thereby accelerate the broken strand away from the hypodermic cylinder 27 so that the free end thereof substantially contacts and adheres to the forming graft 28 in order to form a reattached portion 29. Formation of reattached portion 29 is facilitated by virtue of the fact that the rapid acceleration caused by the electrostatic force directs the fiber to the mandrel and enhances the ability of the broken end to reach the forming vascular graft cylinder 28 before the polymeric fibers have set, which is typically while the extruded polymeric material still includes enough unevaporated solvent so as to maintain same in a highly viscous or tacky condition that promotes fiber adhesion. Without application of the electrostatic field in this regard, the free end dangling from the distributor 21 will pendulum into the other fibers causing additional fiber breakage.

In the embodiment illustrated in FIGS. 5, 6 and 7, the vascular graft cylinder 28a includes a substantially smooth inner surface 31 which is composed of polymeric fibers 22 that had been extruded in the presence of the electrostatic field and had thus been accelerated onto the mandrel 23 in a relatively highly viscous or tacky state. The fibers are accelerated onto the mandrel at a high velocity and draw down ratio, and they impact upon the mandrel 23 before significant solvent evaporation occurs, which condition can be enhanced by formulating the polymer to have an especially high solvent concentration or a less volatile solvent. The acceleration of the fibers often results in a flattening of at least the mandrel side of the fiber. Subsequent electrostatically accelerated fiber layers are forced into the interstices between underlying fibers in order to form inside surface 31 that has a generally smooth, substantially scraggly-free surface and that has a very small pore size. Polymers that are formulated to have an exceptionally high solvent content can be accelerated onto the mandrel such that the inner surface is no longer porous.

For example, proceeding with fiber drawing within the electrostatic field yields a fiber of small diameter, for example between about 1 and 10 microns. Typical pore sizes in this regard are in the range of 1 to 30 microns. If the electrostatic spinning is proceeded with for too long a period of time, the fibers bond extremely well to underlying fibers thereby decreasing their relative movement, and the resultant vascular graft is too stiff and has poor suturability. A maximum of about 20 passes of a 20 orifice spinnerette, when it is extruding a polymer such as 75 D polyurethane (Upjohn), can be tolerated before the resultant vascular graft is overly stiff. If the electrostatically spun fibers were also used to form the outer portions of the vascular graft, the porosity provided typically would be too small in order to promote good tissue ingrowth after implantation. Accordingly, except for occasional and intermittent electrostatic charging, typically in order to achieve fiber reattachment upon breakage, the bulk of the outer layers of polymeric fibers 22 are wound over the inner surface fibers in the absence of the electrostatic field so as to form a substantially porous outer surface 32. The porous surface 32 includes a porous portion having a thickness as desired and as needed to promote tissue ingrowth thereinto when the vascular graft is implanted.

Preferably, the electrostatic field is applied during winding of the last few (e.g. 3) passes on the outer surface of the graft to prevent the outer surface from becoming scraggly when it is handled. However, excessive electrostatically assisted passes on the outer surface causes stiffening of the graft and reduced pore size.

The polymeric material from which the fibers 22 are extruded must be a fiber forming type of polymer; that is, the polymer must be capable of being formed as a fiber when extruded through a fine orifice and into the air. For example, polyamides such as the nylons and regenerated cellulose products such as the rayons are fiber forming. However, many currently available fiber forming polymers are unsuitable for implantation uses or do not possess the properties needed for a flexible graft, such as reasonable pliability, elasticity and biocompatibility. Such polymeric materials also should form viscous solutions in volatile solvents from which continuous fibers may be withdrawn. As a general class of polymers, the polyurethanes tend to possess the physical properties that are desirable for the manufacture of vascular grafts. However, segmented polyurethanes as a class are typically not looked upon as being fiber forming in air, and when extruded they tend to exhibit excessive breakage. Nevertheless polyurethanes of the type that are fiber forming are generally preferred.

Vascular grafts 28 made according to the invention may vary in dimensions as desired. The inside diameter will depend upon the size of the mandrel, a typical range being as fine as a diameter of 0.001 inch, with a practical upper limit being on the order of 2 inches or more, the larger sized grafts being suitable, for example, to be cut into flat sheets or otherwise shaped for making gauze types of products, shunts, bladders, sewing rings and patches, diaphragms and the like. More usual inside diameters can range between about 1 mm to about 50 mm. The size and shape of the pores defined by the fibers from layer to layer of fibers may be controlled by the angle subtended by the fibers with respect to the mandrel, as well as the thickness of the fibers.

The wall thickness of the graft cylinder 28 is also varied as desired and is determined by the number of layers of windings formed on the mandrel and the thickness of the individual wound fibers. The graft thickness is also controlled by the adhesion between subsequent layers of fibers. If the fiber is wet, the next fiber that is layered upon it will sink into the wet fiber, requiring more fiber passes to reach a desired diameter. The electrostatic field causes fibers to sink into underlying fibers by reason of the forces caused by acceleration of the fibers toward the mandrel. The thickness of each fiber winding layer is controlled by the ratio of the flow rate of polymer solution and the relative speed of movement between the distributor 21 and the mandrel 23 and by the extent that the electrostatic charge is applied.

For example, a vascular graft having an inner diameter of approximately 6 mm that is prepared to have a structure generally along the lines of that illustrated in FIGS. 5, 6 and 7, will be made by applying the electrostatic force during spinning until a windings layer having a wall thickness of about 50 microns is formed. Such a layer minimizes scragglyness of the inner lumen or surface 31 and decreases the pore size thereof. The remainder of the windings are applied until the desired wall thickness and porosity are attained, during which procedure the electrostatic field is generated only as needed to rejoin breaks in the fiber forming polymer. Typically, the electrostatic field that is generated and utilized in accordance with this invention is between about 1 and about 40 Kilovolts, preferably about 20 Kilovolts (microamp current).

In another example, a vascular graft having an inside diameter of approximately 4 mm has its interior smooth surface or lumen layer having a plurality of windings that provide a wall thickness of between 1 to 500 microns in order to form a smooth inner surface that will support a very thin (1 micron or less) hemosloughable surface or drug. This can include a substantially nonporous inner surface that is formed from an exceptionally dilute polymer solution which virtually splatters against the mandrel during spinning in order to substantially eliminate intersticies at its innermost surface.

It will be understood that the embodiments of the present invention which have been described are illustrative of some of the applications of the principles of the present invention. Numerous modifications may be made by those skilled in the art without departing from the true spirit and scope of the invention.

We claim:

1. A method of forming biocompatible vascular graft, comprising:
   extruding a continuous fiber forming biocompatible polymeric material through an orifice in order to form an elongated fiber;
   winding said elongated fiber on a mandrel such that the continuous fiber forms a plurality of windings that define a non-woven cylinder having overlying fibers that contact one another;
   intermittently applying an electrostatic charge between said extrusion orifice and said mandrel, said intermittent electrostatic force application procedure including accelerating the elongated fiber onto the mandrel by applying the electrostatic charge between the extrusion orifice and the mandrel after a time period when said winding is carried out in the absence of the electrostatic charge;
   at least a portion of said winding procedure that is carried out on at least certain outer ones of said plurality of windings is carried out in the absence of said electrostatic charge after a time period when said winding is carried out under the influence of the electrostatic charge between the extrusion orifice and the mandrel in order to form a substantially porous outer surface that is conducive to tissue ingrowth thereinto after the vascular graft is implanted;
   observing breakage of the continuous fiber during said winding procedure and applying the electrostatic charge as soon as possible after such breakage occurs for the purpose of accelerating the broken fiber toward the mandrel to reattach the free end to the graft and ceasing to apply such electrostatic charge once such reattachment has been accomplished; and
   removing said non-woven cylinder from said mandrel to provide said biocompatible vascular graft.

2. The method according to claim 1, wherein said intermittent electrostatic charge applying procedure includes forming a substantially smooth inner surface of said non-woven cylinder by applying the electrostatic charge during the extrusion and winding of at least the innermost one of said plurality of windings in order to form said substantially smooth inner surface with a porosity less than that of said substantially porous outer surface.

3. The method according to claim 2, wherein said intermittent electrostatic charge applying procedure includes applying the electrostatic charge to more than one of said innermost plurality of windings and thereby forcing fibers into intersticies between underlying fibers.

4. The method according to claim 1, wherein said intermittent electrostatic charge applying procedure further includes forming a substantially smooth inner surface of said non-woven cylinder by applying the electrostatic charge during the extrusion and winding of at least the innermost one of said plurality of windings in order to form said substantially smooth inner surface with a porosity less than that of said substantially porous outer surface.

5. The method according to claim 1, wherein said winding procedure includes drawing said formed continuous fiber by applying a drawing force longitudinally of the fiber.

6. The method according to claim 1, wherein the extrusion orifice has a diameter larger than the intended diameter of fibers to be drawn therefrom, and said winding procedure includes drawing said fibers drawn from said extrusion orifice by applying a drawing force longitudinally of the fiber.

7. The method according to claim 1, wherein said winding procedure includes providing fiber-to-fiber bonding between overlying fibers.

8. The method according to claim 1, wherein said fiber forming biocompatible polymeric material is a viscous solution of polymeric fiber forming material that produces fiber-to-fiber bonding between overlying fibers during said winding procedure by removal of said solvent therefrom.

9. The method according to claim 1, wherein said fiber forming biocompatible polymeric material is a viscous solution of polyurethane fiber forming material that produces fiber-to-fiber bonding between overlying fibers during said winding procedure by removal of said solvent therefrom.

10. The method according to claim 2, wherein said substantially smooth inner surface is substantially non-porous or has a porosity that is not conducive to tissue ingrowth but is conducive to cell ingrowth thereinto after the vascular graft is implanted.

11. The method according to claim 10, wherein said substantially smooth inner surface has a porosity of not greater than about 50 microns.

12. The method according to claim 2, wherein said substantially smooth inner surface includes a plurality of said windings and has a wall thickness of between about 1 and 500 microns.

13. The method according to claim 1, wherein said intermittent electrostatic charge applying step includes applying the electrostatic charge during at least the outermost winding.

* * * * *

UNITED STATES PATENT AND TRADEMARK OFFICE
CERTIFICATE OF CORRECTION

PATENT NO. : 4,738,740

DATED : April 19, 1988

INVENTOR(S) : Pinchuk et al.

It is certified that error appears in the above-identified patent and that said Letters Patent is hereby corrected as shown below:

Col. 2, line 57, "scraggylness" should read --scraggliness--.

Signed and Sealed this

Sixth Day of December, 1988

Attest:

DONALD J. QUIGG

Attesting Officer

Commissioner of Patents and Trademarks